United States Patent
Zhang et al.

(10) Patent No.: US 12,083,686 B2
(45) Date of Patent: Sep. 10, 2024

(54) ARTICULATION JOINT HARDSTOP HANDLING FOR SURGICAL TOOL

(71) Applicant: Verb Surgical Inc., Santa Clara, CA (US)

(72) Inventors: Xiaobin Zhang, Santa Clara, CA (US); Dimitri Chatzigeorgiou, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 1011 days.

(21) Appl. No.: 17/063,298

(22) Filed: Oct. 5, 2020

(65) Prior Publication Data

US 2022/0105638 A1    Apr. 7, 2022

(51) Int. Cl.
| | |
|---|---|
| B25J 9/16 | (2006.01) |
| A61B 34/00 | (2016.01) |
| A61B 34/35 | (2016.01) |
| B25J 13/06 | (2006.01) |
| A61B 17/072 | (2006.01) |
| A61B 90/00 | (2016.01) |

(52) U.S. Cl.
CPC ............. *B25J 9/1689* (2013.01); *A61B 34/25* (2016.02); *A61B 34/35* (2016.02); *B25J 13/06* (2013.01); *A61B 2017/07285* (2013.01); *A61B 2034/742* (2016.02); *A61B 2034/743* (2016.02); *A61B 2034/744* (2016.02); *A61B 2090/066* (2016.02); *A61B 90/37* (2016.02)

(58) Field of Classification Search
CPC ......... B25J 9/1689; B25J 13/06; A61B 34/25; A61B 34/35; A61B 2034/742; A61B 2034/743; A61B 2034/744; A61B 2090/066; A61B 90/37; A61B 2017/07285

USPC ............................................................ 606/1
See application file for complete search history.

(56) References Cited

U.S. PATENT DOCUMENTS

| | | |
|---|---|---|
| 6,981,628 B2 | 1/2006 | Wales |
| 8,224,484 B2 | 7/2012 | Swarup et al. |
| (Continued) | | |

FOREIGN PATENT DOCUMENTS

| | | |
|---|---|---|
| CN | 111730594 A | 10/2020 |
| WO | 2015142907 A1 | 9/2015 |
| (Continued) | | |

OTHER PUBLICATIONS

International Search Report and Written Opinion for International App. No. PCT/IB2021/059041 mailed Dec. 30, 2021.

*Primary Examiner* — Aaron F Roane
(74) *Attorney, Agent, or Firm* — Lempia Summerfield Katz LLC

(57) ABSTRACT

The disclosed embodiments relate to systems and methods for a surgical tool or a surgical robotic system. One example system for handling hardstops includes one or more processors configured to calculate an articulation joint position for the articulation drive disk or the one or more corresponding rotary motors corresponding rotary motors, calculate an articulation joint torque for the articulation drive disk or the one or more corresponding rotary motors, determine a torque ratio based on the articulation joint position and the articulation joint torque, and adjust a commanded articulation joint position received from the user based on the torque ratio to compensate for collision involving the end effector.

20 Claims, 14 Drawing Sheets

(56) References Cited

U.S. PATENT DOCUMENTS

| | | | |
|---|---|---|---|
| 8,245,898 B2 | 8/2012 | Smith | |
| 9,439,649 B2 | 9/2016 | Shelton, IV | |
| 10,145,747 B1* | 12/2018 | Lin | A61B 90/06 |
| 2019/0125455 A1* | 5/2019 | Shelton, IV | A61B 17/072 |
| 2019/0261988 A1* | 8/2019 | Weir | A61B 17/07207 |
| 2019/0274769 A1* | 9/2019 | Perdue | A61B 34/35 |

FOREIGN PATENT DOCUMENTS

| | | |
|---|---|---|
| WO | 2020028356 A1 | 2/2020 |
| WO | 2020040796 A1 | 2/2020 |

* cited by examiner

ARTICULATION JOINT HARDSTOP HANDLING FOR SURGICAL TOOL

FIELD

This disclosure relates to hardstop detection and handling during operation of a surgical tool.

BACKGROUND

Minimally invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more surgical tools (e.g., end effectors and endoscope) through the incisions into the patient. The surgical procedures may then be performed using the introduced surgical tools, with the visualization aid provided by the endoscope.

Generally, MIS provides multiple benefits, such as reduced patient scarring, less patient pain, shorter patient recovery periods, and lower medical treatment costs associated with patient recovery. Recent technology development allows more MIS to be performed with robotic systems that include one or more robotic arms for manipulating surgical tools based on commands from a remote operator. A robotic arm may, for example, support at its distal end various devices such as surgical end effectors, imaging devices, cannulae for providing access to the patient's body cavity and organs, etc. In robotic MIS systems, it may be desirable to establish and maintain high positional accuracy for surgical instruments supported by the robotic arms.

In some example, the surgical end effectors may contact a hardstop in the body or elsewhere. The hardstop may be a part of the body or another substantially rigid object that the end effector contacts. While some systems provide feedback to the user regarding contact with a hardstop, other system may provide no feedback or only video. It may be impossible to identify the hardstop with no feedback and difficult to identify the hardstop with only video. The following disclosure provides system, apparatus, and method for the identification of hardstops and handling of hardstops by a surgical tool.

SUMMARY

Disclosed herein is a robotically assisted surgical electromechanical system designed for surgeons to perform minimally invasive surgery. A suite of compatible tools can be attached/detached from an instrument driver mounted to the distal end of a robotic arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints.

One example apparatus to compensate for collision between an end effector of a surgical tool and a hardstop includes a tool driver and one or more processors. The tool driver is connected by a shaft to the end effector and has at least an articulation drive disk driven by one or more corresponding rotary motors. The articulation drive disk corresponds to an articulation motion of the end effector in a plane corresponding to a longitudinal axis of the shaft connecting the tool driver to the end effector. The one or more processors are configured to calculate an articulation joint position for the articulation drive disk or the one or more corresponding rotary motors, calculate an articulation joint torque for the articulation drive disk or the one or more corresponding rotary motors, determine a torque ratio based on the articulation joint position and the articulation joint torque, and calculate an articulation joint adjustment, for the articulation drive disk or the one or more corresponding rotary motors, in response to the torque ratio to compensate for a hardstop.

One example method to compensate for collision between an end effector of a surgical tool and a hardstop includes calculating an articulation joint position for the articulation drive disk or the one or more corresponding rotary motors corresponding rotary motors for an articulation motion of the end effector in a plane corresponding to a longitudinal axis of a shaft connecting the end effector, calculating an articulation joint torque for the articulation drive disk or the one or more corresponding rotary motors corresponding rotary motors, determining a torque ratio based on the articulation joint position and the articulation joint torque, and calculating an articulation joint adjustment in response to the torque ratio to compensate for a hardstop.

DETAILED DESCRIPTION

The following embodiments relate to control systems for a robotic endoscopic surgical instrument. Endoscopic surgical instruments typically include a long, thin tube that is inserted directly into the body to observe or otherwise perform a task on an internal organ or tissue. Endoscopic surgical instruments may be inserted through an incision or other opening of the body such as the mouth or anus. Endoscopic surgical instruments may be suitable for precise placement of a robotic distal end effector at a desired surgical site through a cannula. These robotic distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, radio frequency (RF) treatment, lasers, or others).

As in many surgical instruments, one problem faced by endoscopic instruments is in the handling of a hardstop. The hardstop may be a rigid surface or object that could block the robotic end effector to move and prevent it from following the user's input command. The term hardstop may alternatively refer to a collision with the object. It could be an external rigid object or the robotic end-effector internal mechanical hard stop itself. When the robotic end-effector is hitting a hardstop, the user may not be able to identify the hardstop. For example, when only visual feedback is available, the user may not identify the hardstop because the hardstop is inside the patient's body. In that situation, the user may still command the robotic end effector to move further against the hard stop. But since the end effector cannot move, the extra joint command from the user may be converted into a further motor displacement/command that attempts to move the end effector further against the hardstop and could lead to the damage of the robot's mechanical structure or external object.

The following embodiments solve this problem and allow the surgical instrument's articulation joint to collide with a hardstop, which may be internal or external to the instrument, safely without any damage to the robot and/or the external object.

Figure 1:
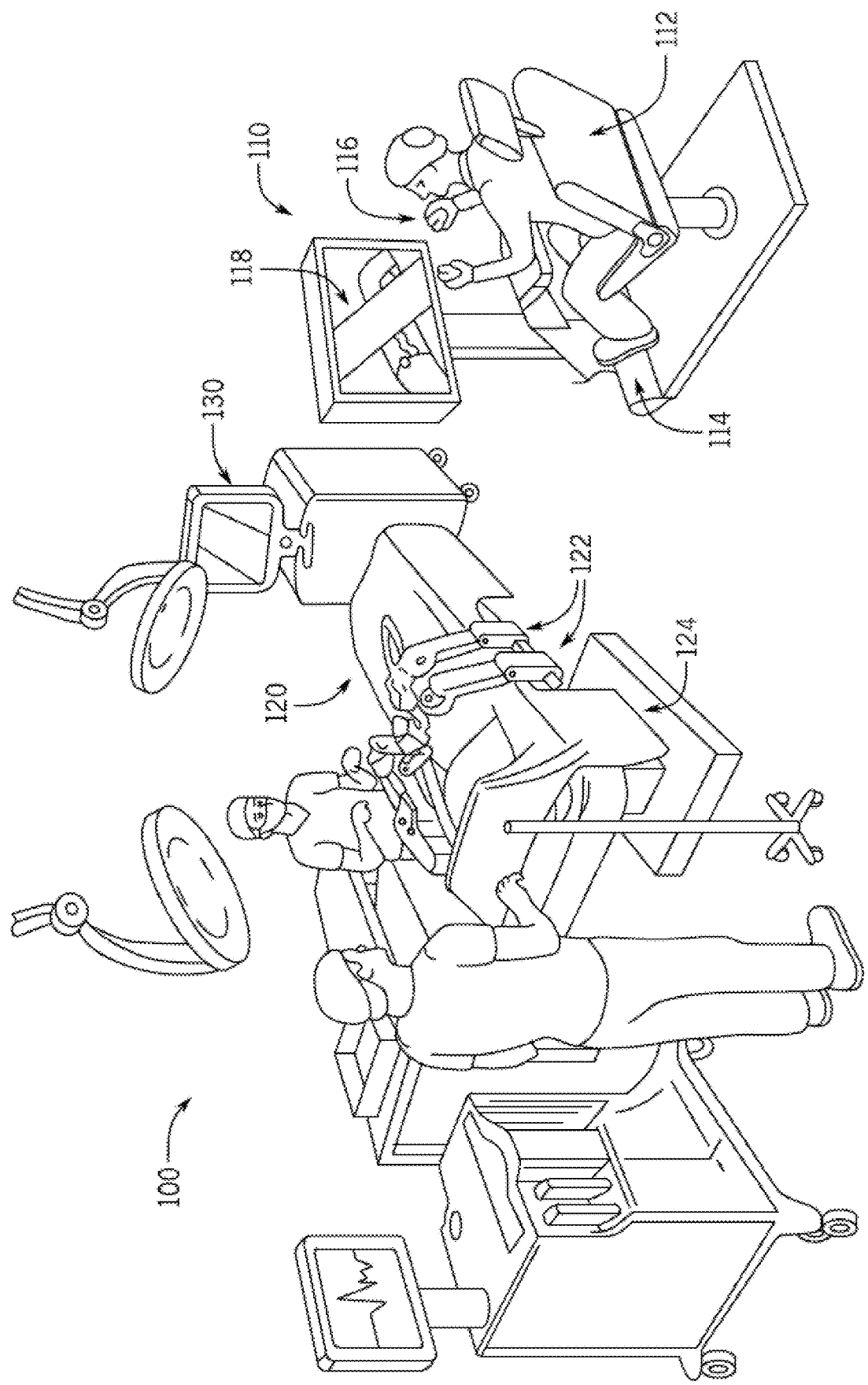
FIG. 1 illustrates an example operating room environment including a surgical robotic system.

FIG. 1 is a diagram illustrating an example operating room environment with a surgical robotic system 100. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. The robotic arms 122 are shown as table-mounted, but other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or teleoperated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic assisted minimally invasive surgery (MIS) and manual laparoscopic surgery on a patient.

An end effector may be configured to execute a surgical operation such as cutting, grasping, poking, or energy emission. The surgical tool may be manipulated manually, robotically, or both, during the surgery. For example, the surgical tool may be a tool used to enter, view, or manipulate an internal anatomy of the patient. In an embodiment, the surgical tool is a grasper that can grasp tissue of the patient. The surgical tool may be controlled manually, directly by a hand of a bedside operator or it may be controlled robotically, via sending electronic commands to actuate movement.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues, or performing manual repositioning or tool exchange involving one or more robotic arms 122. Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The surgical platform 124 and robotic arms 122 may be in a fully stowed configuration with the arms 122 under the surgical platform 124 for storage and/or transportation purposes. The surgical team can extend the arms from their stowed position for sterile draping.

After draping, the arms 122 can be partially retracted until needed for use. A number of conventional laparoscopic steps may be performed including trocar placement and installation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars.

After insufflation, if required, manual instruments can be inserted through the sleeve to perform any laparoscopic steps by hand. Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The surgical platform 124 can be repositioned intraoperatively. For safety reasons, all tooltips should be in view and under active control by the surgeon at the user console 110. Instruments that are not under active surgeon control are removed, and the table feet are locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

Figure 2:
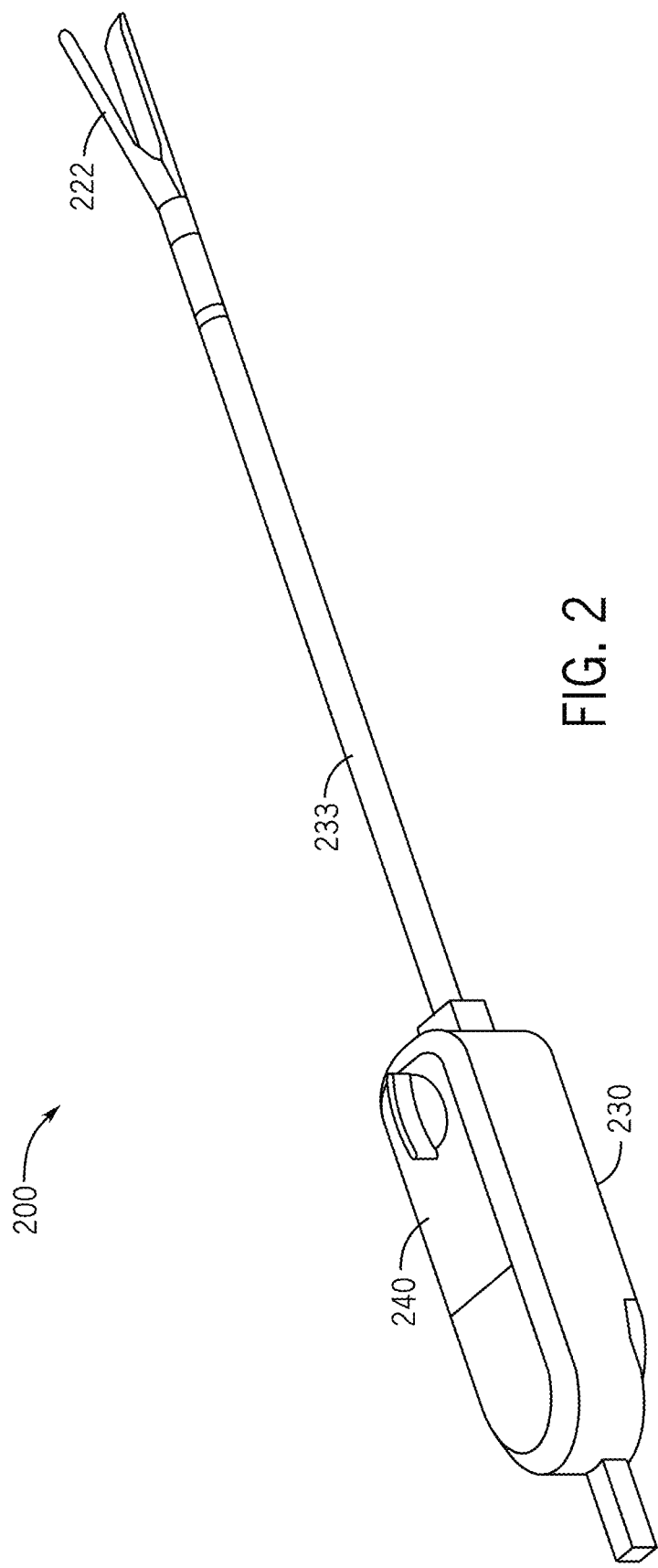
FIG. 2 illustrates an example surgical tool.

FIG. 2 illustrates an example surgical tool assembly 200. The surgical tool assembly 200 includes a surgical tool 240 to a tool driver 230. The surgical tool 240 is connected to end effector 222 via shaft 233. Additional, different, or fewer components may be included.

The surgical tool assembly 200 may be an endoscopic surgical instrument. The surgical tool assembly 200 may be an endocutter. An endocutter may be configured to divide and seal tissue. Put another way, an endocutter may be configured to cut and staple tissue with motion provided by an articulation joint. The endocutter may be used to cut and staple tissue in a variety of surgical procedures, including bariatric, thoracic, colorectal, gynecologic, urologic, and general surgery. Common clinical use scenarios include reshaping organs, the removal or repair of organs, tissue fixation, dissection, or the creation of anastomoses (or any combination of these).

FIG. 2 is an illustration of a subsystem or a part of the surgical robotic system 100, for detecting engagement of a surgical tool 240 to a tool driver 230 of a surgical robotic arm 122. The surgical robotic arm 122 may be one of the surgical robotic arms of surgical robotic system 100 illustrated and discussed with respect to FIG. 1. The control unit 210 may be part of for example the control tower in FIG. 1. As discussed in more detail herein, the engagement may be detected by control unit 210 based on one or more rotary motor operating parameters of one or more actuators (e.g., actuator 238-$j$) in the tool driver 230.

There is a tool driver 230 to which different surgical tools (e.g., surgical tool 240, as well as other detachable surgical tools for rotation of an endoscope camera, pivoting of a grasper jaw, or translation of a needle) may be selectively attached (one at a time.) This may be done by for example a human user holding the housing of the surgical tool 240 in her hand and moving the latter in the direction of arrow 280 shown until the outside surface of the surgical tool 240 in which there are one or more tool disks (e.g., tool disk 244-$i$ described below) comes into contact with the outside surface of the tool driver 230 in which there are one or more drive disks (e.g., drive disk 234-$j$ described below). The one or more tool disks and/or one or more drive disks may be implemented by pucks, which may be formed of plastic or another durable material. In the example shown, the tool driver 230 is a segment of the surgical robotic arm 122 at a distal end portion of the surgical robotic arm 122. A proximal end portion of the arm is secured to a surgical robotic platform, such as a surgical table that shown in FIG. 1 described above.

The control system is described in detail with respect to FIG. 12 below. By of introduction to the control system, the control system of FIG. 12 includes a control unit 210 configured to control motion of the various motorized joints in the surgical robotic arm 122 (including the drive disks 234) through which operation of end effector 222 (its position and orientation as well as its surgical function such as opening, closing, cutting, applying pressure, etc.) which mimics that of a user input device is achieved. This is achieved via a mechanical transmission in the surgical tool 240, when the surgical tool 240 has been engaged to transfer force or torque from the tool driver 230. The control unit 210 may be implemented as a programmed processor, for example as part of the control tower 130 of FIG. 1. It may respond to one or more user commands received via a local or remote user input (e.g., joystick, touch control, wearable device, or other user input device communicating via console computer system.) Alternatively, the control unit 210 may respond to one or more autonomous commands or controls (e.g., received form a trained surgical machine learning model that is being executed by the control unit 210 or by the console computer system), or a combination thereof. The commands dictate the movement of robotic arm 122 and operation of its attached end effector 222.

An end effector 222 may be any surgical instruments, such as jaws, a cutting tool, an endoscope, spreader, implant tool, stapler, etc. FIG. 2 includes an endocutter having a combination of two or more of these instruments such as a cutting tool, jaws, and stapler. Different surgical tools each having different end effectors can be selectively attached (one at a time) to robotic arm 122 for use during a surgical or other medical procedure.

The robotic arm includes a tool driver 230, in which there are one or more actuators, such as actuator 238-j. Each actuator may be a linear or rotary actuator that has one or more respective electric motors (e.g., a brushless permanent magnet motor) whose drive shaft may be coupled to a respective drive disk 234-j through a transmission (e.g., a gear train that achieves a given gear reduction ratio). The tool driver 230 includes one or more drive disks 234 that may be arranged on a planar or flat surface of the tool driver 230, wherein the figure shows several such drive disks that are arranged on the same plane of the flat surface. Each drive disk (e.g., drive disk 234-j) is exposed on the outside surface of the tool driver 230 and is designed to mechanically engage (e.g., to securely fasten via snap, friction, or other mating features) a mating tool disk 244-j of the surgical tool 240, to enable direct torque transfer between the two. This may take place once for example a planar or flat surface of the surgical tool 240 and corresponding or mating planar or flat surface of the tool driver 230 are brought in contact with one another.

Furthermore, a motor driver circuit (for example, installed in the tool driver 230 or elsewhere in the surgical robotic arm 122) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-j).

When the mating drive disk 234-j is mechanically engaged to a respective tool disk 244-j, the powered rotation of the drive disk 234-j causes the tool disk 244-j to rotate, e.g., the two disks may rotate as one, thereby imparting motion on, for example, linkages, gears, cables, chains, or other transmission devices within the surgical tool 240 for controlling the movement and operation of the end effector 222 which may be mechanically coupled to the transmission device.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 222 to achieve goals such as load sharing by two or more motors that are driving the mating drive disks 234, respectively. In another aspect, within the tool driver 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complementary actions in the same degree of freedom, e.g., a first drive disk 234-j rotates a drum within the housing of the surgical tool 240 to take in one end of a rod, and a second drive disk 234-i rotates another drum within the housing of the surgical tool 240 to take in the other end of the rod. As another example, the extension and the shortening of an end effector along a single axis may be achieved using two tool disks 234-i, 234-j, one to perform the extension and another to perform the retraction. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 222 being jaws, two or more tool disks 244 may cooperatively control the motion of the jaws, for load sharing, as discussed in greater detail herein.

In yet another aspect, within the surgical tool 240, there may be a transmission which translates torque from two drive disks 234 (via respective tool disks 244) for performing complimentary actions in the same degree of freedom, e.g., a first drive disk 234-i rotates a drum within the housing of the surgical tool 240 to take in one end of a cable, and a second drive disk 234-j rotates another drum within the housing of the surgical tool 240 to take in the other end of the cable. As another example, the extension and the shortening of an end effector along a single axis may be achieved using two tool disks 234-i, 234-j, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

Figure 3:
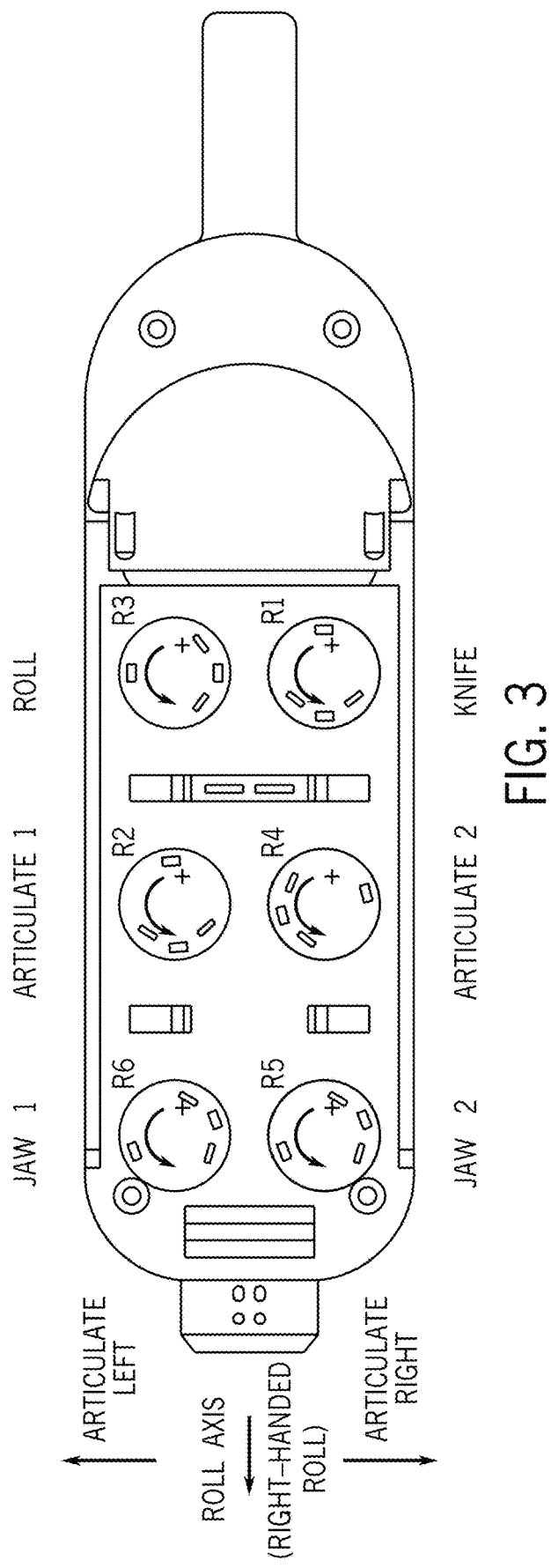
FIG. 3 illustrates a mapping for the tool driver to the surgical tool.

FIG. 3 illustrates a mapping for the tool driver 230 to the surgical tool 240. FIG. 3 illustrates rotary device assignments or mapping for tool disks R1-R6. In this example, tool disk R1 is assigned to a cutting instrument such as a knife. As the tool disk R1 is moved in one direction (e.g., clockwise) the cutting instrument advances, and as the tool disk R1 is moved in a second direction (e.g., counterclockwise) the cutting instrument retracts.

Tool disks R2 and R4 are assigned to the articulation joint. The tool disks R2 and R4 may be connected to the end effector 222 in an antagonistic pairs, that is, when one cable of the antagonistic pair is actuated or tensioned, while the other cable is loosened, the jaw will rotate in one direction. When only the other cable is tensioned, the jaw will rotate in an opposite direction. One direction (e.g., clockwise) corresponds to articulation of the end effector 222 to the left, and the other direction (e.g., counterclockwise) corresponds to the articulation of the end effector to the right. Articulation may be a change in orientation of the end effector 222 at an axis transverse to the longitudinal axis of the shaft of the instrument. This articulated positioning permits the clinician to more easily engage tissue in some instances. In addition, articulated positioning advantageously allows an endoscope to be positioned behind the end effector without being blocked by the instrument shaft.

Tool disk R3 is mapped to the roll axis of the end effector. The tool disk R3 may be coupled to one or more gears that drive the wrist to rotate about the roll axis. The rotation of the tool disk R1 in a first direction with respect to the plane of the tool disks (e.g., clockwise) may cause rotation of the roll axis of the end effector in the same direction (e.g., clockwise) and rotation of the tool disk R1 in a second direction with respect to the plane of the tool disks (e.g., counter clockwise) may cause rotation of the roll axis of the end effector in the same direction (e.g., counter clockwise).

Tool disks R5 and R6 are assigned to the closure device or jaw. For example, the one of the opposing jaws may be assigned to tool disk R5 and tool disk R6 operation in one direction for opening the jaw (i.e., increasing the angle between the opposing jaws) and another direction for closing the jaw (i.e., decreasing the angle between the opposing jaws).

In some embodiments, when surgical tool 240 is first attached to or installed on tool driver 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, radio frequency identification (RFID) tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-*e, f, g, h, i, j*), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool driver 230 may include a communication interface 232 (e.g., a memory writer, a near field communications, near field communication (NFC), transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool driver 230 may also include a corresponding sensor for each possible information storage unit that would be present in a given tool.

After surgical tool 240 is attached with tool driver 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool driver 230 is now deemed engaged with the tool). That is, attaching the surgical tool 240 with the tool driver 230 does not necessarily ensure the proper mating needed for mechanical engagement of tool disks with corresponding drive disks (e.g., due to misalignment of mating features). The engagement process may include activating one or more motors of an actuator (e.g., actuator 238-*j*) that drives a corresponding drive disk 234-*j*. Then, based on one or more monitored motor operating parameters of the actuator 238-*j*, while the latter is driving the drive disk 234-*j*, the mechanical engagement of the tool disk 244-*i* with a drive disk 234-*j* can be detected. This process may be repeated for every drive disk 234 (of the tool driver 230) that is expected to be currently attached to a respective tool disk 244 (e.g., as determined based on the tool disk information obtained for the particular surgical tool 240 that is currently attached.)

Upon detecting that a particular type of surgical tool 240 has been attached with the tool driver 230, the control unit 210 activates one or more actuators (e.g., motors) of the tool driver 230 that have been previously associated with that type of surgical tool 240. In some embodiments, each actuator that is associated with a corresponding drive disk 234 of surgical tool 240 may be activated simultaneously, serially, or a combination of simultaneous and serial activation.

Figure 4:
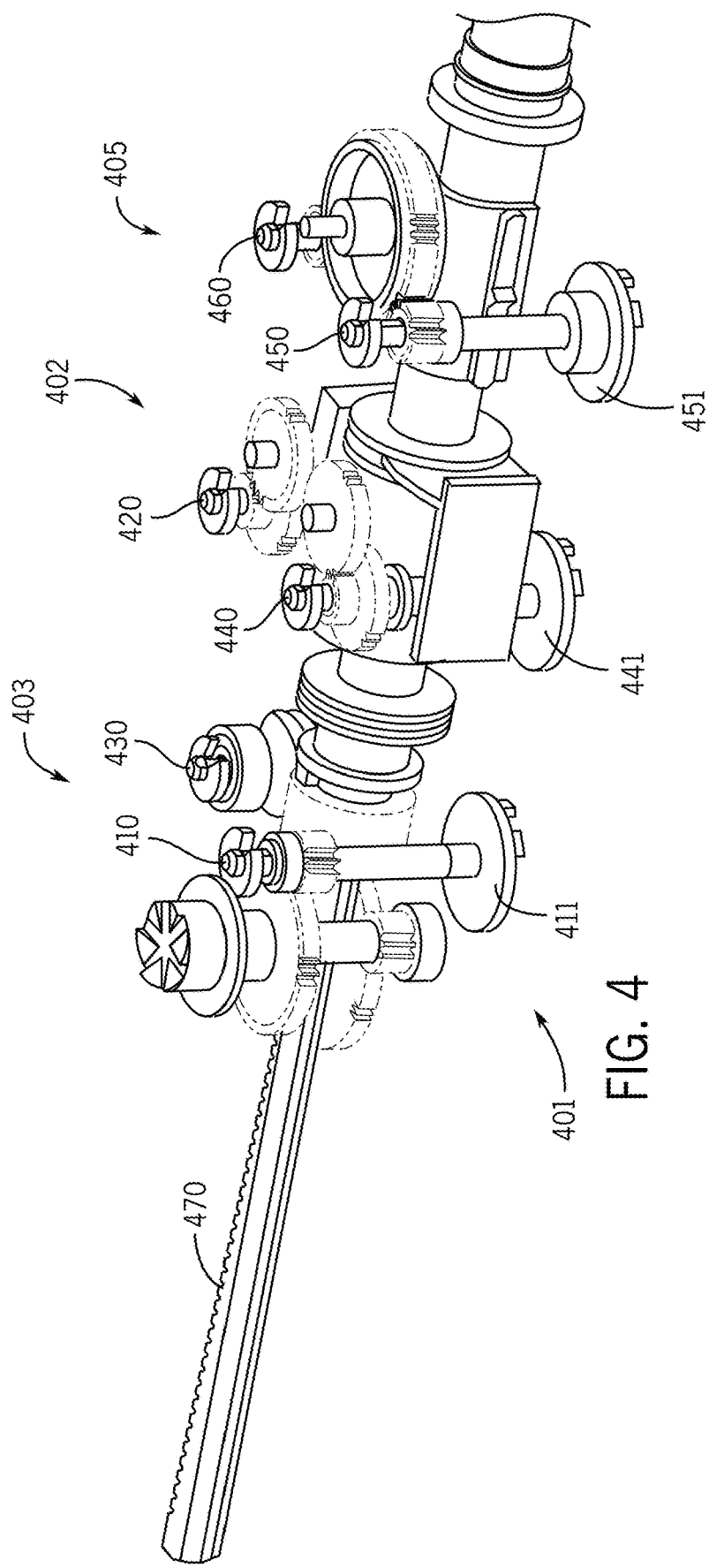
FIG. 4 illustrates a view of a drive system for the surgical tool.
Figure 5:
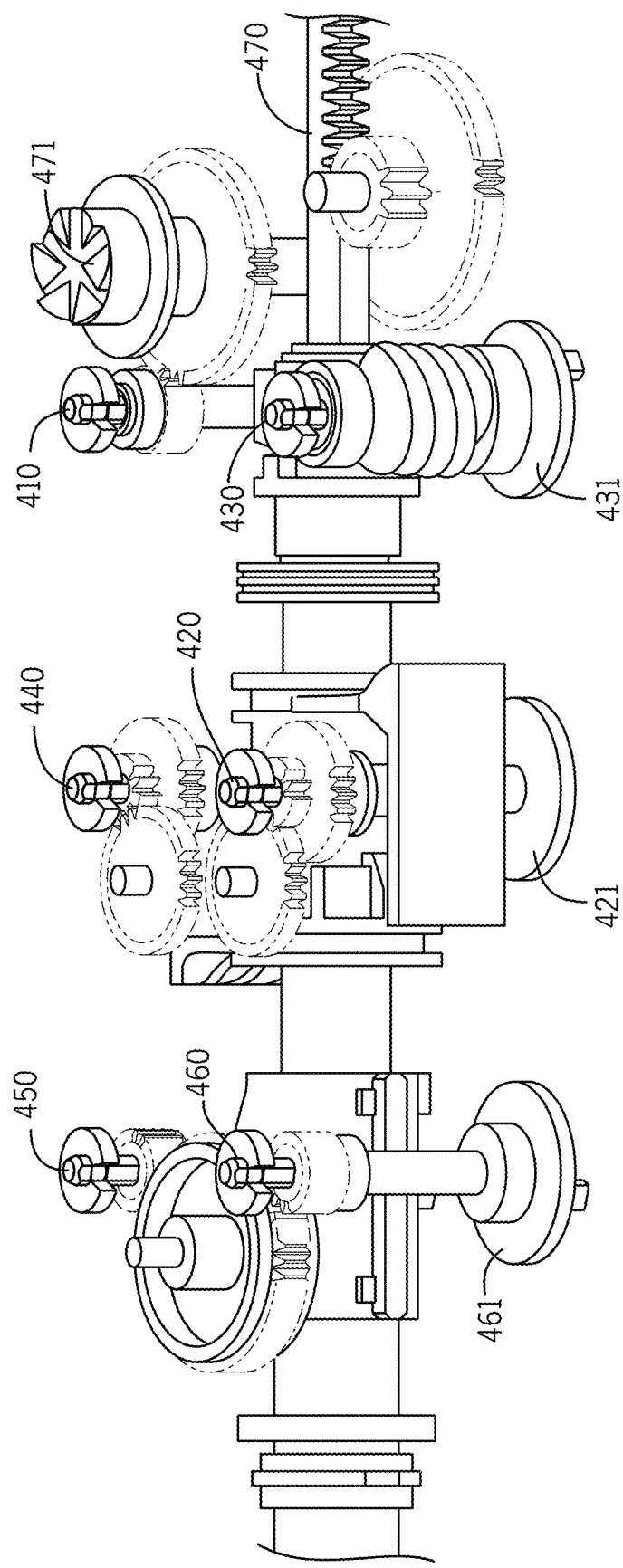
FIG. 5 illustrates another view of a drive system for the surgical tool.

FIGS. 4-11 illustrate a drive system for the surgical tool 240. FIG. 4 illustrates a left side view of a drive system for the surgical tool and FIG. 5 illustrates a right-side view of the drive system. The drive system includes a fire subsystem 401, an articulation subsystem 402, a roll subsystem 403, and a closure subsystem 405. Additional, different, or fewer components may be included.

Figure 6:
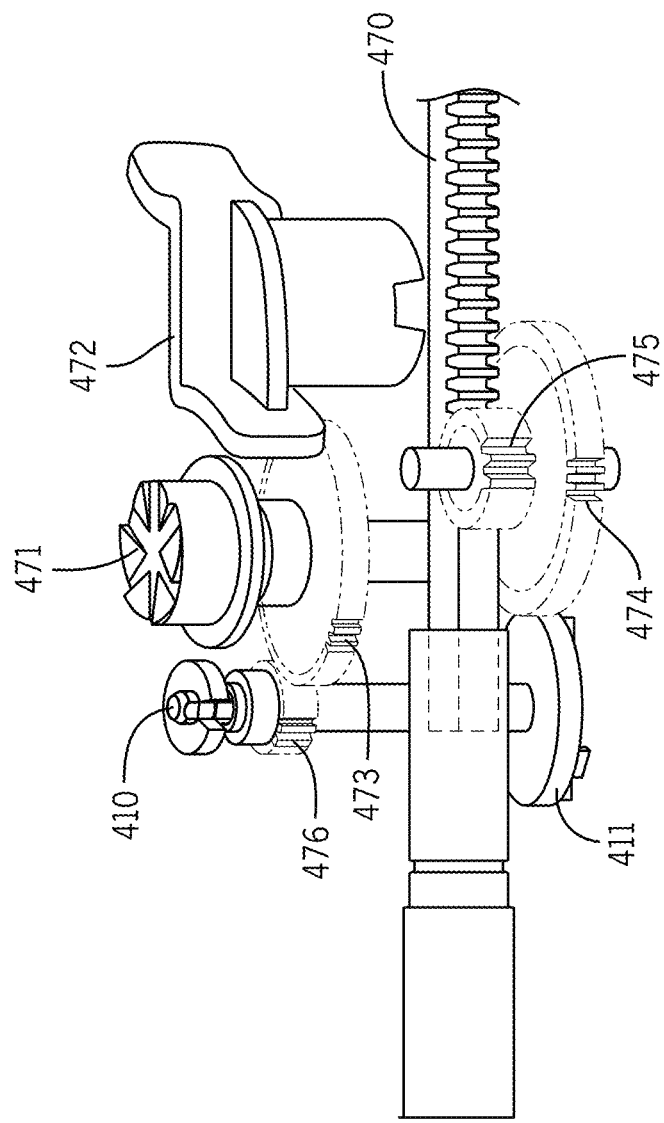
FIG. 6 illustrates a firing subsystem of the drive system for the surgical tool.

FIG. 6 illustrates the firing subsystem 401 of the drive system for the surgical tool. The fire subsystem 401 includes a firing shaft 410 that is rigidly connected to tool disk R1 (firing input puck 411). The firing shaft 410 may be coupled to and support the firing input puck 411 such that the firing input puck 411 is mounted to the firing shaft 410. Also mounted to the firing shaft 410 may be a driving gear 476 (firing shaft driving gear). The driving gear 476 imparts motion and torque onto driven gear 473. The driven gear 473 is part of the drive train to the drive bar 470 and also facilitates the bailout mechanism. The rest of the drive train to the drive bar 470 includes a gear reduction set including gear 474 driven by the shaft of the driven gear 473 and a pinion gear 475 that runs along the rack of the drive bar 470.

The bailout mechanism includes a manual bailout input cylinder 471. The user input device 472 fits over the manual bailout input cylinder 471 or is otherwise coupled to the manual bailout input cylinder 471. Rotating the manual bailout input cylinder 471 through user input a portion of the drive train out of engagement with the drive bar 470. This manually overrides the movement of the drive bar 470 from the tool driver 230.

Figure 7:
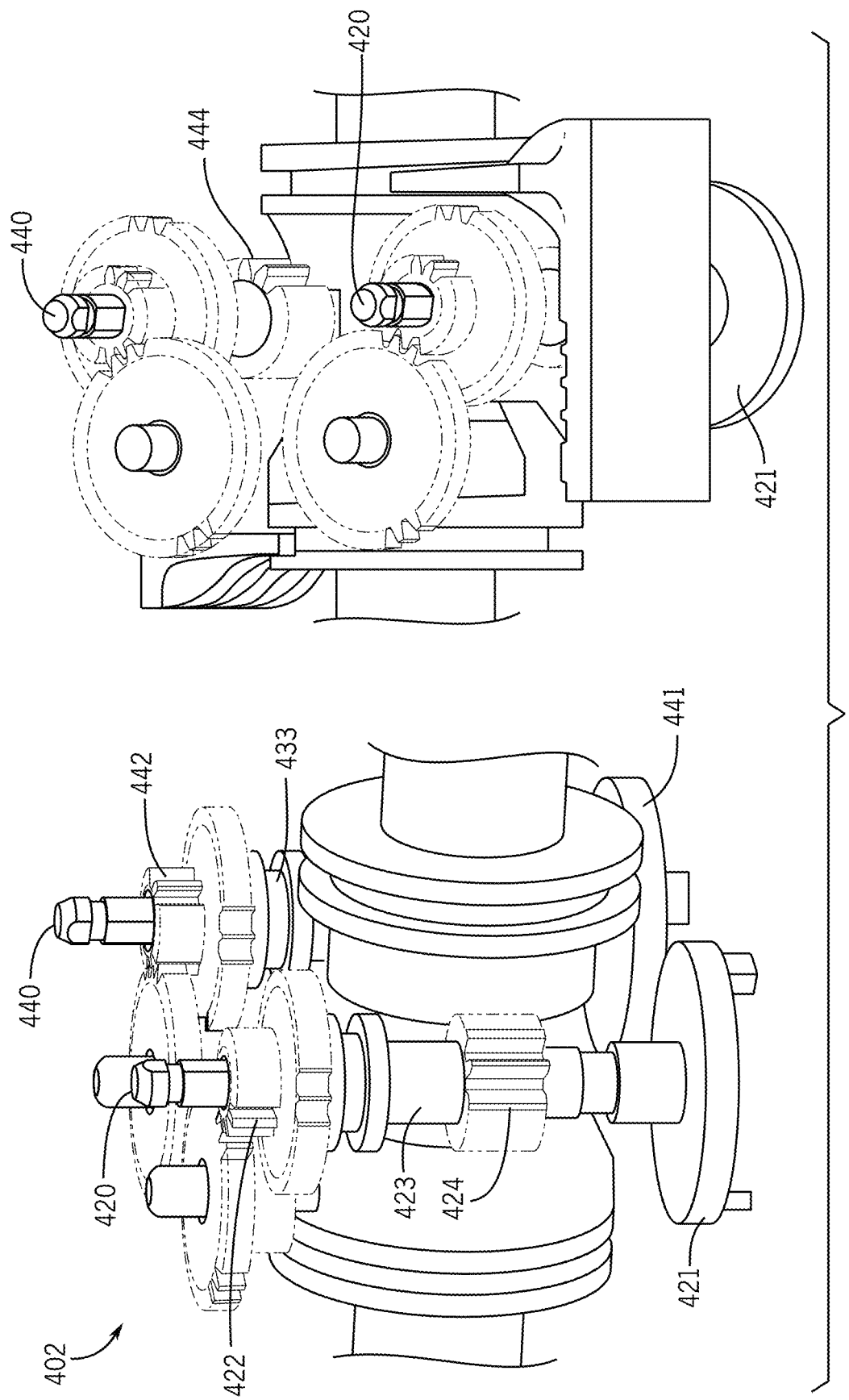
FIG. 7 illustrates an articulation subsystem of the drive system for the surgical tool.
Figure 8:
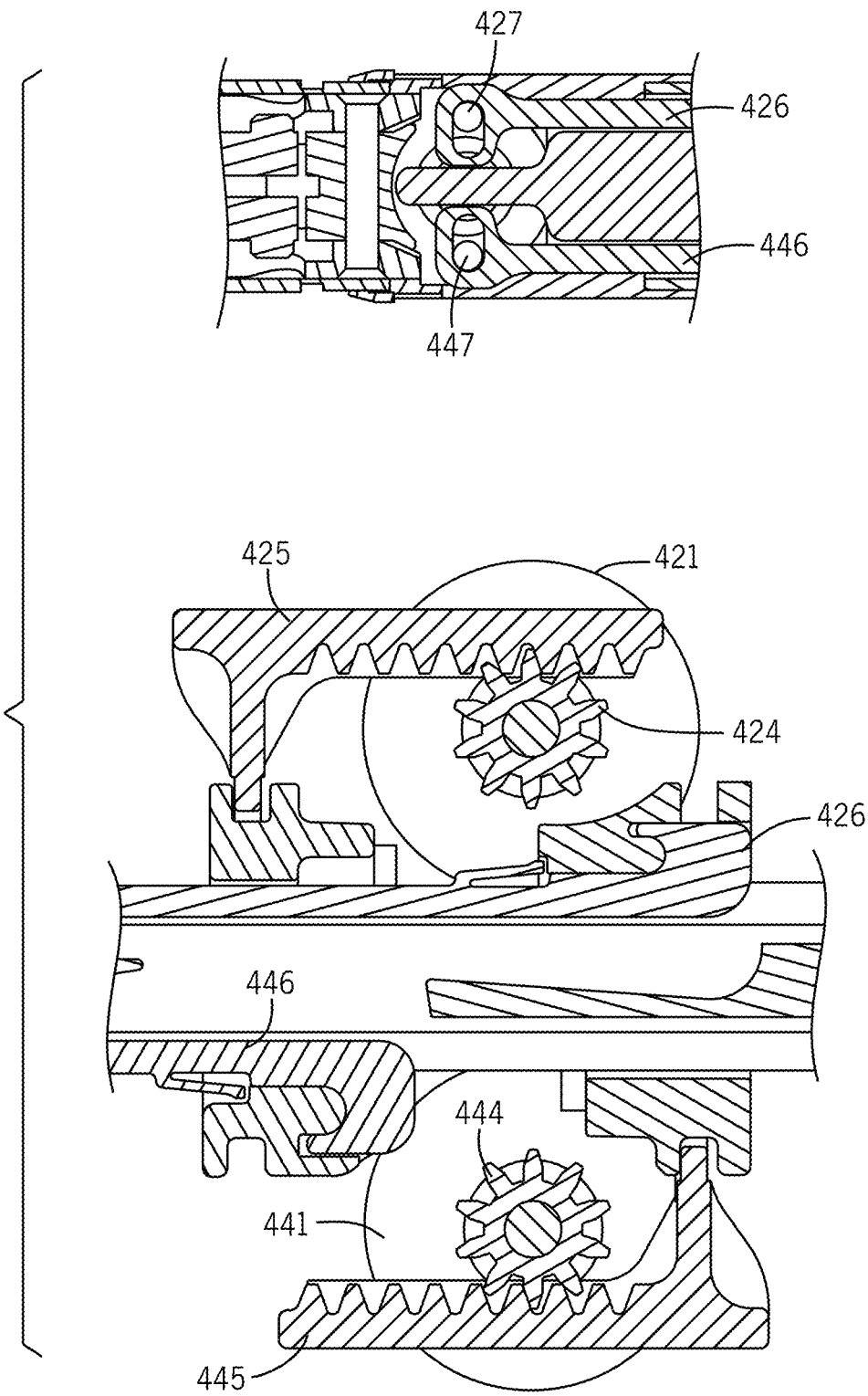
FIG. 8 illustrates a top down view of the articulation subsystem.

FIG. 7 illustrates the articulation subsystem 402 of the drive system for the surgical tool. FIG. 8 illustrates a top down view of the articulation subsystem 402. The articulation subsystem 402 includes a left articulation shaft 440 and a right articulation shaft 420. The left articulation shaft 440 is coupled to and driven by tool disk R4 (left articulation input puck 441). The right articulation shaft 420 is coupled to and driven by tool disk R2 (right articulation input puck 421). The left articulation shaft 440 includes a left pinion gear 444 connected to the articulation joint. The right articulation shaft 420 includes a right pinion gear 420 connected to the articulation joint.

FIG. 8 provides more detail of the drive of the articulation joint. Right pinion gear 424 drives right rack 425 connected to the articulation joint. Left pinion gear 444 drives left rack 445 connection to the articulation joint. The right rack 425

(e.g, first rigid rod) moves the right articulation arm 426 and ultimately causes the right protrusion 427 of the articulation joint to rotate about the center of the articulation disk. Likewise, the left rack 445 (e.g., second rigid rod) moves the left articulation arm 446 and ultimately causes the left protrusion 447 of the articulation joint to rotate about the center of the articulation disk. Movement of the right rack 425 and/or the left rack 445 applies torques at the wrist to create articulation movement.

The tool driver 230 include at least one articulation drive disk driven by one or more corresponding rotary motors, and the articulation drive disk corresponds to an articulation motion of the end effector in a plane corresponding to a longitudinal axis of the shaft connecting the tool driver 230 to the end effector.

Figure 9:
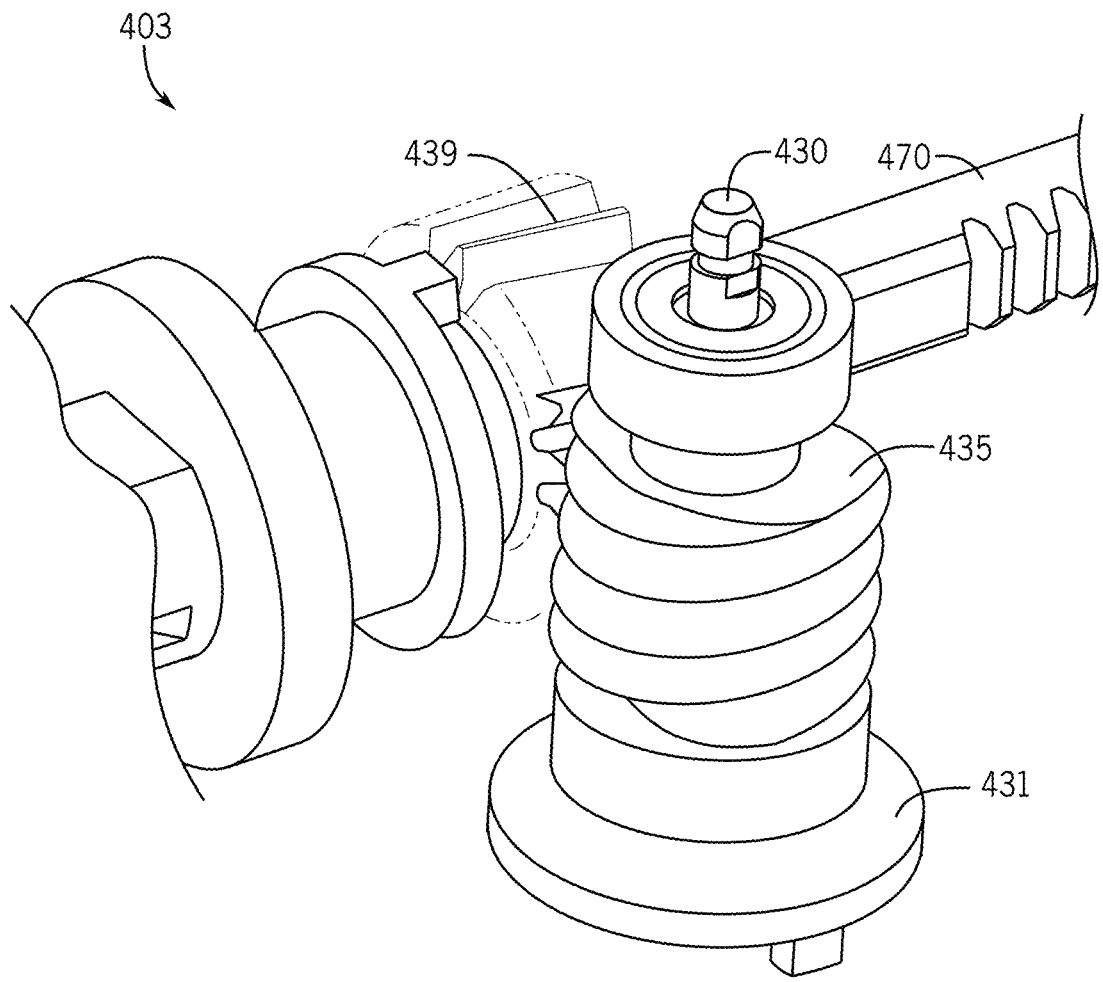
FIG. 9 illustrates a roll subsystem of the drive system for the surgical tool.

FIG. 9 illustrates the roll subsystem 403 of the drive system for the surgical tool. The roll subsystem 403 includes a roll shaft 430. The roll shaft 430 is coupled to and driven by tool disk R3 (roll input puck 431). The roll input puck 431 is coupled to the roll shaft 430 along with worm gear 435 in order to drive roll gear 439. The roll gear 439 provides the motion to the roll joint in either the clockwise or counterclockwise direction depending on the rotation of the tool disk R3.

Figure 10:
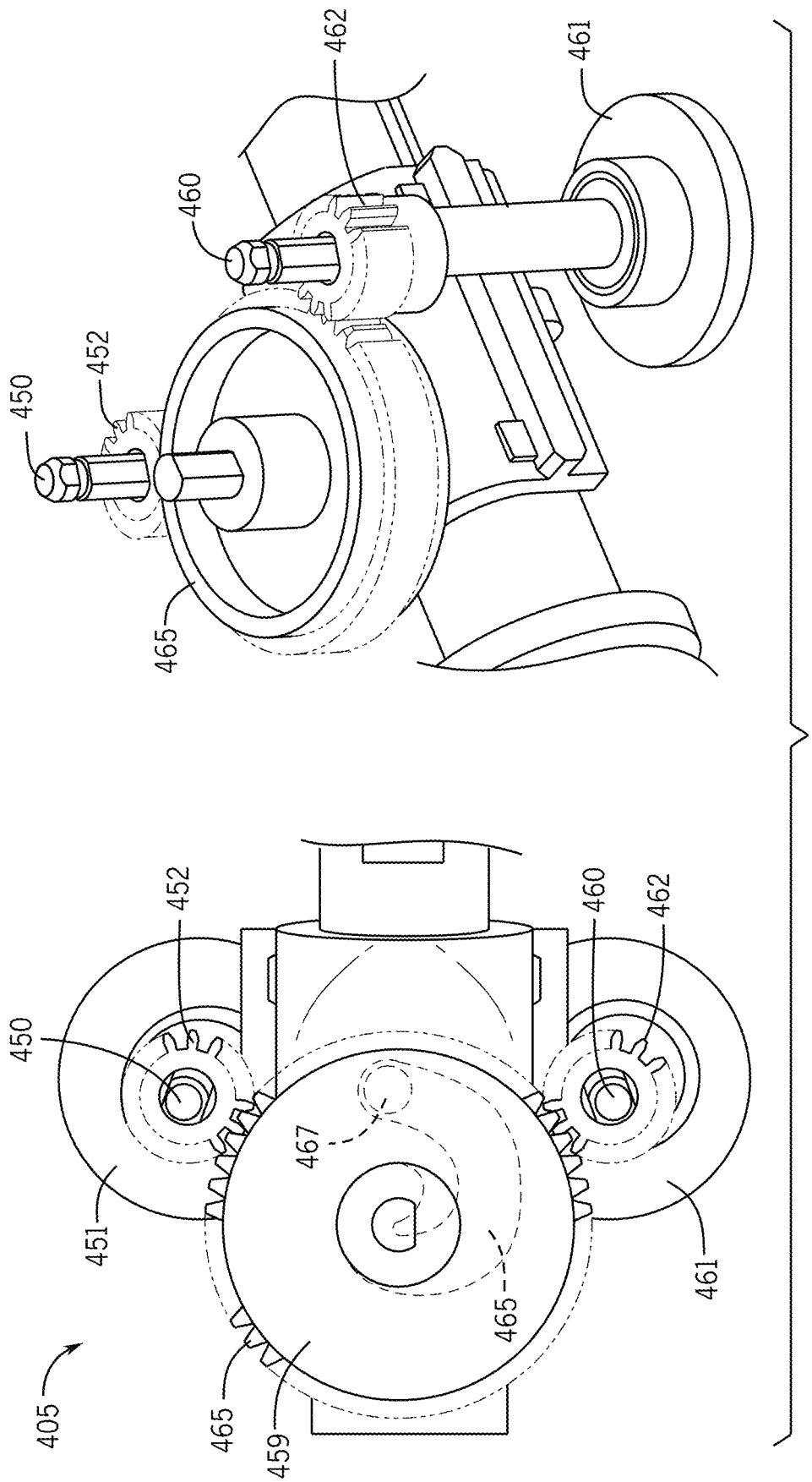
FIG. 10 illustrates a closure subsystem of the drive system for the surgical tool.

FIG. 10 illustrates a closure subsystem 405 of the drive system for the surgical tool. The closure subsystem 405 includes a left closure shaft 450 and a right closure shaft 460. The left closure shaft 450 is coupled to and driven by tool disk R5 (left closure input puck 451). The right closure shaft 460 is coupled to and driven by tool disk R6 (right closure input puck 461). A left drive gear 452 is coupled to the left closure shaft 450 and a right drive gear 462 is coupled to the right closure shaft 460. The left drive gear 452 and the right drive gear 462 cooperate to drive closure gear 465, which operates the closure joint.

A cam cam/yoke mechanism 459 translates the rotary input from the left closure input puck 451 and the right closure input puck 461 to a linear output. A variable mechanical advantage is provided by the cam/yoke mechanism 459 at a function of its angular position. For example, the cam/yoke mechanism 459 may include a push pull rod that distally includes a pin 467 that slides on a slot 468, creating the open close jaw motion.

Figure 11:
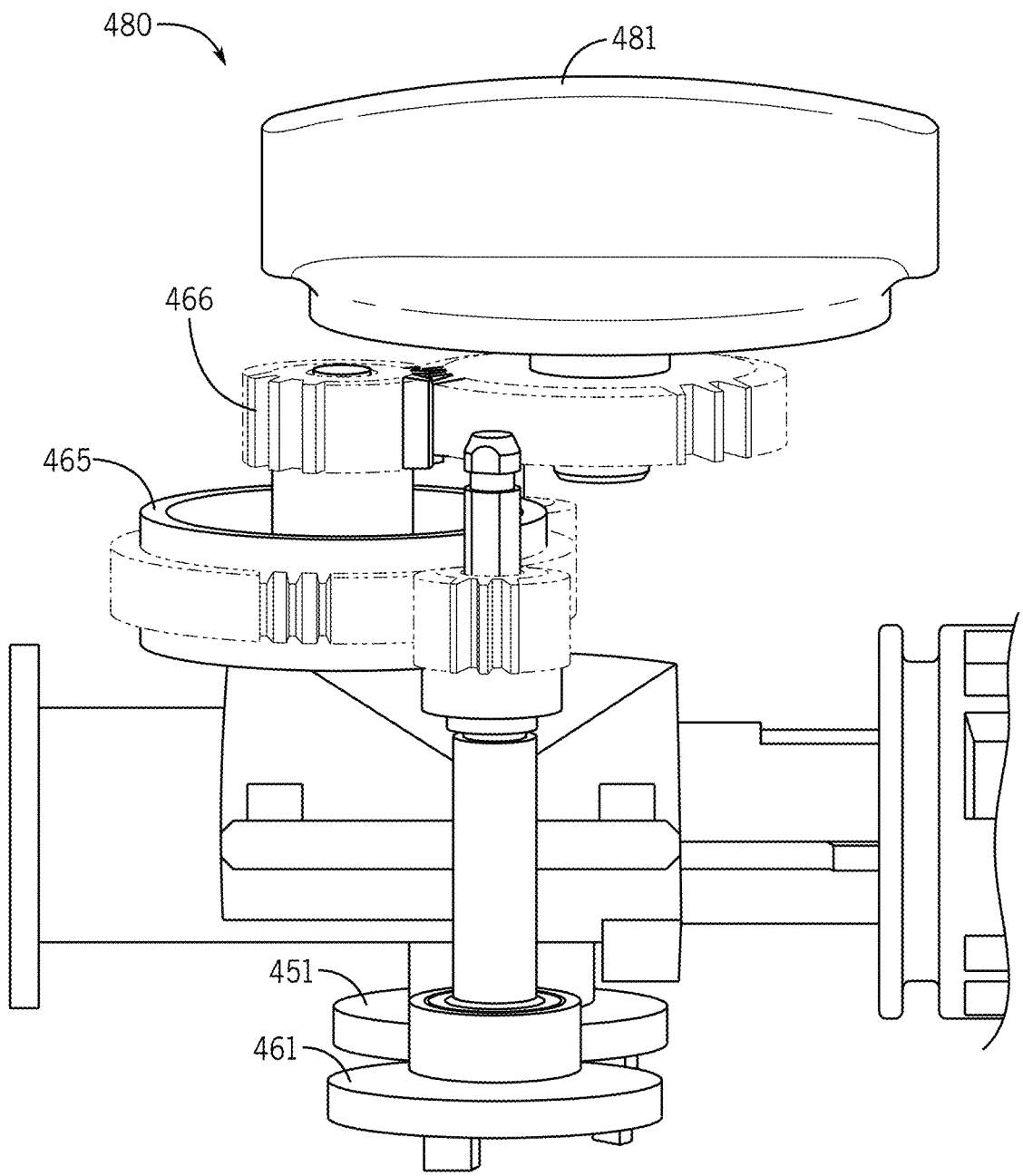
FIG. 11 illustrates a manual knob for the closure subsystem.

FIG. 11 illustrates a manual knob 481 for the closure subsystem 405. One or more coupling gears 466 couple the drive closure gear 465 to the manual know 481. The manual knob 481 includes a surface or handle for receiving a user's grip to rotate the manual knob 481, causing rotation of the left drive gear 452 and/or the right drive gear 462, to manually operate the closure joint.

Figure 12:
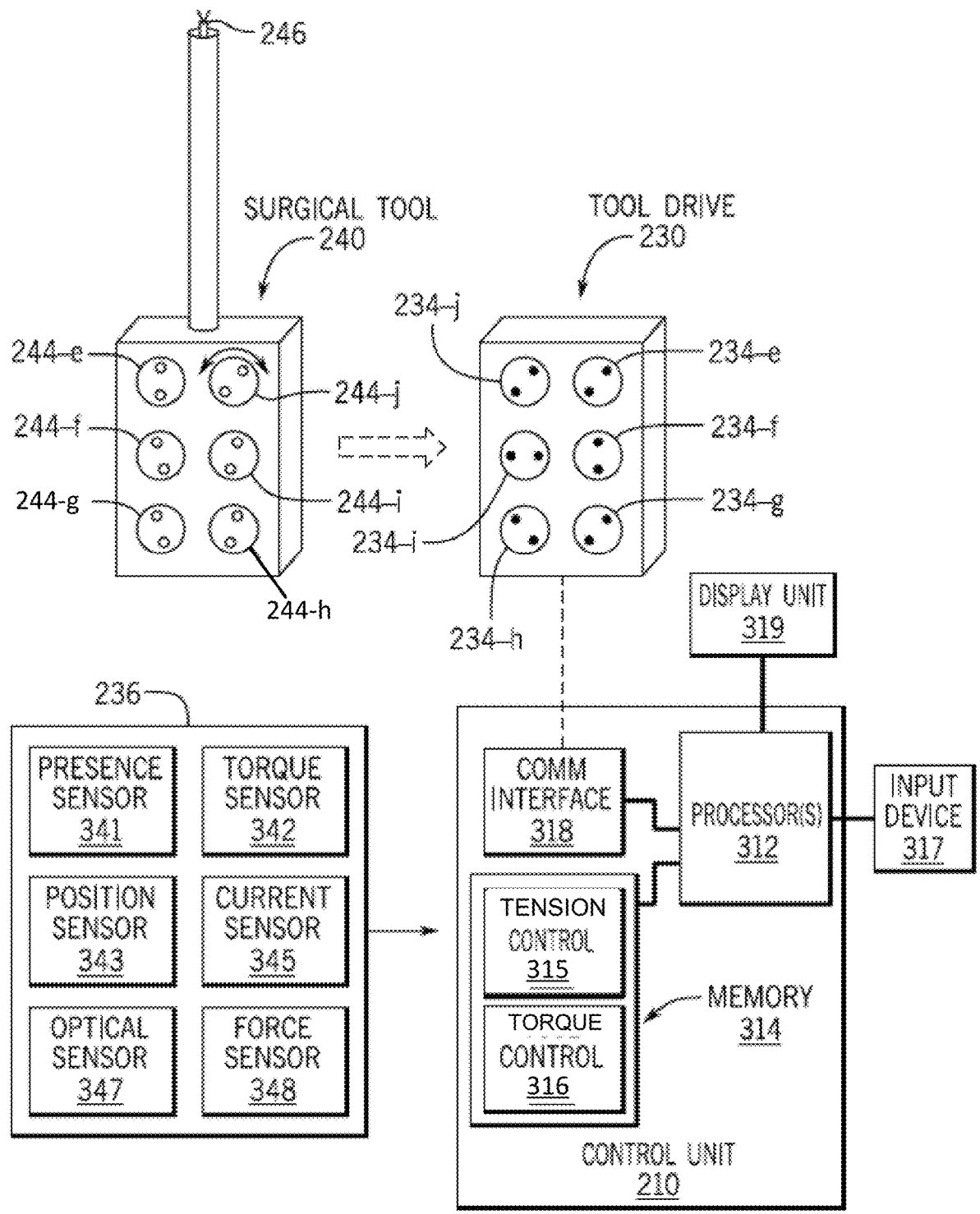
FIG. 12 illustrates a controller for the tool driver and/or surgical tool.

FIG. 12 illustrates an example of the surgical tool 240 that utilizes six tool disks, such as tool disks 244-*e, f, g, h, i, j*, arranged in a coplanar fashion on a mating surface of its housing. Any arrangement of tool disks 244-*e, f, g, h, i, j*, may correspond to tool disks R1-R6, in general, or specifically firing input puck 411, right articulation input puck 421, roll input puck 431, left articulation input puck 441, left closure input puck 451, and right closure input puck 461 described previously. Each tool disk contributes to at least a portion of the movement and/or activation of end effector 222. Upon detecting the attachment of surgical tool 240 with tool driver 230 (e.g., joining of mating surfaces of the respective housings), control unit 210 (or its processor 312 while executing instructions stored in memory 314 as) performs a process which determines that the corresponding drive disks, such as drive disks 234 *e, f, g, h, i, j*, are to be turned (a corresponding actuator 238 is activated) to perform the engagement process.

In some embodiments, the motor operating parameters monitored by the control unit 210 (via sensors 236) are interpreted to mean successful mechanical engagement of a tool disk with a drive disk. The control unit 210 is in communication with and receives sensor data from sensor 236 in an example sensor array including any combination of a presence sensor 341, a torque sensor 342, a position sensor 343, an electrical sensor 345, an optical sensor 347, and a force sensor 348. The sensor array may include separate sensors for different degrees of freedom of the surgical tool (e.g., closure joint, articulation joint, roll joint, or other operation of the surgical tool). That is, the sensor array, or one or more sensors thereof, may be repeated for multiple tool disks 244 in the tool driver 230.

The measurements may include measurements of torque applied by the actuator 238-*j* as measured by the torque sensor 342 or the force sensor 348, measurements of current by the electrical sensor 345 supplied to a motor of the actuator 238-*j* when attempting to drive the actuator to move at a certain velocity (e.g., where the sensor 236-*j* may include a current sensing resistor in series with a motor input drive terminal), measurements of electrical impedance by the electrical sensor 345 as seen into the input drive terminals of the motor of the actuator 238 when attempting to drive the motor to move at a certain velocity (e.g., where the sensor 236-*j* may also include a voltage sensing circuit to measure voltage of the motor input drive terminal), speed of the actuator 238-*j* (e.g., where the optical sensor 347 may include a position encoder on an output shaft of the actuator 238-*j* or on a drive shaft of the motor), as well as other parameters referred to here as motor operating parameters. The measurements may include presence data from the presence sensor 341, implied from any sensor in the sensor array 236, or determined from the interaction between the information storage unit 242 and the communication interface 232. The position sensor 343 is illustrated separately but may be implemented using a combination of the presence sensor 341, the torque sensor 342, the electrical sensor 345, the optical sensor 347, and the force sensor 348. In one example, additional sensors of the same type may be used for the position sensor 343.

While monitoring the one or more motor operating parameters of a particular actuator, when one or more of these parameters satisfies (e.g., meets or reaches) a predetermined, condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-*j* or that is part of another actuator 238-*i* which his being controlled by the control unit 210 simultaneously during the engagement detection process.

In some embodiments, detection of certain motor operating parameters during operation of the actuator 238-*j*, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-*j* to drive disk 234-*j* has occurred.

The control unit 210 including its programmed processor 312 may be integrated into the surgical robotic system 100 (FIG. 1) for example as a shared microprocessor and program memory within the control tower 130. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached surgical tool 240, a power device (e.g., a battery), as well as other components typically associated with electronic devices for controlling surgical robotic systems.

Memory 314 is coupled to one or more processors 312 (generically referred to here as a processor for simplicity) to store instructions for execution by the processor 312. In some embodiments, the memory is non-transitory, and may store one or more program modules, including a tension control algorithm 315 and a torque control algorithm 316, whose instructions configure the processor 312 to perform the tension and torque control algorithms 315 and 316 as described herein. In other words, the processor 312 may operate under the control of a program, routine, or the execution of instructions stored in the memory 314 as part of the tension control algorithm 315 and the torque control algorithm 316 to execute methods or processes in accordance with the aspects and features described herein. The memory 314 may include one or more settings, coefficient values, threshold values, tolerance values, calibration values for the surgical tool 240 and/or the tool driver 230. These values may be stored in memory 314 as a configuration file, table, or matrix. Some values in the configuration file may be provided by the user, some may be accessed or retrieved based on identifiers of the surgical tool 240 or tool driver 230, and others may be set by the control unit 210.

Figure 13:
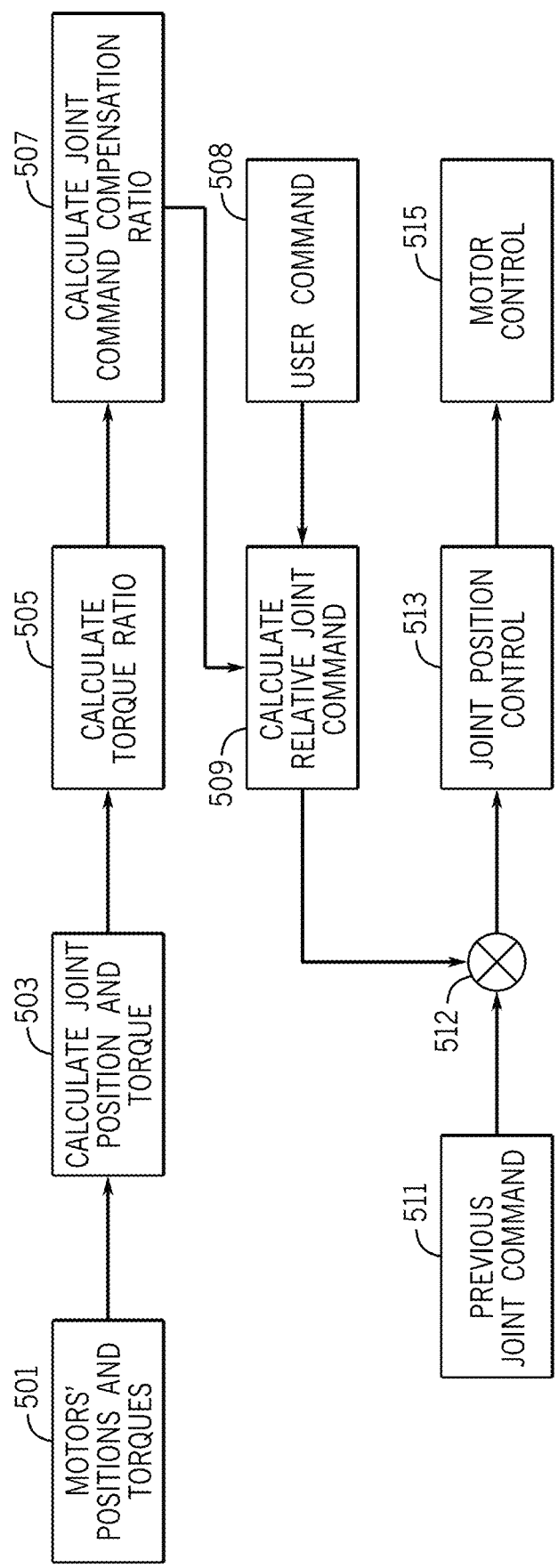
FIG. 13 illustrates an example block diagram for a control system for hardstop control.

FIG. 13 illustrates an example block diagram for a control system for hardstop control, which may be implemented by the control unit 210 to control the one or more actuators in the tool driver 230 to drive one or more tool disks, which in the case of the example articulation joint described herein, includes tool disks R2 and R4. The tool disks R2 and R4 may be connected to sliders that are configured to pull or release a rod. Tool disk R2 pulls in one direction while R4 is released and, at another time, tool disk R4 pulls in another direction while R3 is released. In this way, articulation is controller in two rotation directions.

The control system calculates positions and torques for a joint under analysis. From these values, a torque ratio is determined. When a user input for the joint is received, the control system analyses the state of the joint in light of the torque ratio, to determine how the user input should impact current movement of the joint. Depending on the state of the joint, which is measured in light of a hardstop that the surgical instrument may be contacting, an adjustment or compensation is calculated to either stop the requested movement at the joint or reduce the requested movement at the joint.

At each iteration of the control system, data is received at block 501. The data may include motor positions and motor torques. For example, a torque sensor 342 may measure torques of the corresponding actuators or motors in the tool driver 230 to calculate a torque measurement for tool disk R2 and a torque measurement for tool disk R4. A position sensor 343, or optical sensor 347 with a position encoder), may measure positions of the corresponding actuators or motors in the tool driver 230 to calculate a torque measurement for tool disk R2 and a torque measurement for tool disk R4.

Any of the described sensors may generate sensor data used to determine motor torque. The torque may be directly measured by the associated torque sensor 342 or the force sensor 348 applied to the tool disk or motor. The motor torque may be indirectly measured from current sensed by the electrical sensor 345 supplied to a corresponding motor when attempting to drive the actuator to move at a certain velocity (e.g., a current sensing resistor in series with a motor input drive terminal). The motor torque may be indirectly measured by samples of electrical impedance by the electrical sensor 345 as seen into the input drive terminals of the motor of the actuator 238 when attempting to drive the motor to move at a certain velocity. The motor torque may be indirectly measured by the speed of the tool disk or actuator (e.g., a position encoder on an output shaft of the actuator 238-j or on a drive shaft of the motor).

At block 503, the joint position and joint torques are calculated. The motor positions and motor torques may be measured by the sensors and associated circuitry. The following calculations may be applied to any joint but are discussed with respect to the articulation joint. The control unit 210 may receive sensor data and calculate the articulation joint position for the articulation drive disk or the one or more corresponding rotary motors. The control unit 210 may calculate an articulation joint torque for the articulation drive disk or the one or more corresponding rotary motors corresponding rotary motors. The calculations of the joint position and joint torques may occur repeatedly at a predetermined time unit, described for illustration as time interval k. Thus, for any given time (k), a previous time is k−1 and a subsequent time is k+1.

At block 505, a torque ratio is calculated for the current time interval. The control unit 210 is configured to determine a torque ratio based on the articulation joint position and the articulation joint torque. The articulation joint for the surgical tool 240 is driven by two motors (e.g., the motors correspond to tool disks R2 and R4). The physical displacement of the articulation joint ($\theta_j$) is provided by Equation 1:

$$\theta_j = \sin^{-1} \frac{a + \frac{1}{2}(\theta_{m1} + \theta_{m2})}{b} \qquad \text{Eq. 1}$$

The relationship in Equation 1 is based on a first position ($\theta_{m1}$) for a first actuator or motor (e.g., corresponding to tool disk R2) and a second position ($\theta_{m2}$) for a second actuator or motor (e.g., corresponding to tool disk R4), and at least one property constant including a first constant a and second constant b. The property constant may depend on the materials of the components, the relative dimensions of the components, or other factors. The control unit 210 may lookup the property constants from a table using an identifier for the instrument.

Based on a static force analysis, the motors-to-joint torque map be described by the following relationships. For example, Equation 2 demonstrates a relationship between joint torque ($\tau_j$) and a first motor torque ($\tau_{m1}$) for a first actuator (e.g., corresponding to tool disk R2) and a second motor torque ($\tau_{m2}$) for a second actuator (e.g., corresponding to tool disk R4), and at least one property constant including, for example, the first constant a, the second constant b, or a ratio of two or more property constraints.

$$\tau_j = \frac{b}{a}(\tau_{m1} + \tau_{m2}) * \sqrt{1 - \frac{a}{b}(\tau_{m1} + \tau_{m2})^2} \qquad \text{Eq. 2}$$

Equation 3 describe a torque ratio ($r_\tau$) which may be a number in the range of [−1, 1] and as a function of the physical displacement of the articulation joint ($\theta_j$) and joint torque ($\tau_j$) of the articulation joint. In this way, the articulation joint torque ($\tau_j$) is calculated based on a relationship at least one measured torque for the one or more corresponding rotary motors and at least one property constant for the surgical tool 240. Equation 3, as defined according to the following examples, includes at least one example that is both continuous and differentiable.

$$r_{96} = f(\theta_j, \tau_j) \qquad \text{Eq. 3}$$

Figure 14:
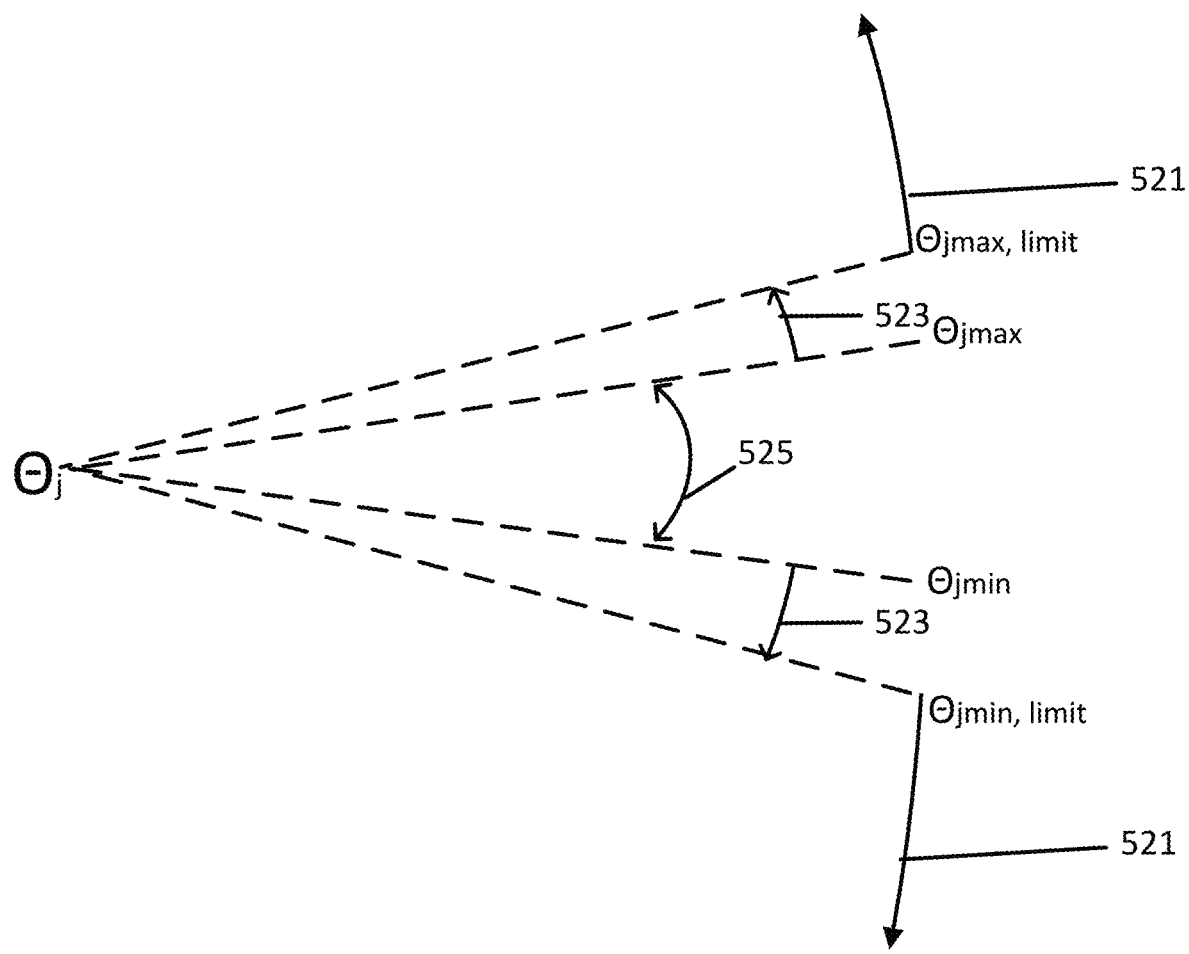
FIG. 14 illustrates angle ranges for a torque ratio determination for the hardstop control of FIG. 13.

FIG. 14 illustrates angle ranges for a torque ratio determination for the hardstop control of FIG. 13. FIG. 14 illustrates angle ranges for a torque ratio determination for the hardstop control of FIG. 13. The articulation joint ($\theta_j$) may be calculated as any angle. The control unit 210 determines which of the angle range that the articulation joint ($\theta_j$) falls within. The angle ranges may include on outer range 523, a middle range 521, and an inner range 521. The inner range 521 may include values for the articulation joint ($\theta_j$) between $\theta_{jmin}$ and $\theta_{jmax}$. In the inner range 521, no compensation may be needed. That is, user commands may not be modified. The inner range 521 may be referred to as the uncompensated range.

The middle range 521 may include value for the articulation joint ($\theta_j$) outside of $\theta_{jmin}$ and $\theta_{jmax}$ but still within the limits of $\theta_{jmin,limit}$ and $\theta_{jmax,limit}$. The middle range 521 may be referred to as a compensation range where compensation is performed. That is, user commands for the joint may be modified but the user commands still impact the movement of the joint.

An outer range 523 includes values outside of $\theta_{jmin,limit}$ and $\theta_{jmax,limit}$. The outer range 523 may be referred to as an out of bounds range. The user commands may be blocked in this out of bounds range. That is, the movement at the joint is not impacted by user commands.

The control unit 210 defines the torque ratio ($r_\tau$) based on the articulation joint ($\theta_j$). Equations 4-9 define the relationship. If the articulation joint ($\theta_j$) is equal to $\theta_{jmin}$ and $\theta_{jmax}$, the torque ratio ($r_\tau$) is zero.

If $\theta_j \Sigma [\theta_{jmin}, \theta_{jmax}], r_\tau = 0$ \qquad Eq. 4

If the articulation joint ($\theta_j$) is outside of the outer range, the torque ratio ($r_\tau$) is set to +1 or −1, as shown by Equations 5 and 6. The torque ratio ($r_\tau$) is set to −1 when the articulation joint ($\theta_j$) is less than $\theta_{jmin,limit}$. The torque ratio ($r_\tau$) is set to 1 when the articulation joint ($\theta_j$) is greater than $\theta_{jmax,limit}$.

If $\theta_j < \theta_{jmin,limit}, r_\tau = -1$ \qquad Eq. 5

If $\theta_j > \theta_{jmax}, \text{limit}, r_\tau = 1$ \qquad Eq. 6

Other limits are defined according to torque limitations of the tool. The limit $\tau_{jnormal}$ is the joint torque limit during normal usage of the surgical tool 240 and $\tau_{jmax}$ is the maximum allowed joint torque to avoid damage of the surgical tool 240. The user may provide values for $\tau_{jnormal}$ and $\tau_{jmax}$ are provided by the user too. If the measured joint torque ($\tau_j$) is less than the limit $\tau_{jnormal}$, then the torque ratio ($r_\tau$) is set to 0, as shown by Equation 7.

If $|\tau_j| < \tau_{jnormal}, r_\tau = 0$ \qquad Eq. 7

If the measured joint torque ($\tau_j$) is greater than the limit $\tau_{jmax}$, then the torque ratio ($r_\tau$) is set to 1, as shown by Equation 8.

If $\tau_j > \tau_{jmax}, r_\tau = 1$ \qquad Eq. 8

If the measured joint torque ($\tau_j$) is less than the limit $-\tau_{jmax}$, then the torque ratio ($r_\tau$) is set to −1, as shown by Equation 9.

If $\tau_j < -\tau_{jmax}, r_\tau = -1$ \qquad Eq. 9

If none of the conditions in Equations 4-9 are true, then Equations 10-13 provide the torque ratio ($r_\tau$). The control unit 210 is configured to calculate a joint position percentage ($\Delta\theta$) when the joint position is within the compensation range bounded by a minimum value ($\theta_{jmin}$) and a maximum value ($\theta_{jmax}$). The joint position percentage ($\Delta\theta$) may not be used when the joint position is within the uncompensated range or the out of bounds range bounded by a minimum limit value ($\theta_{jmin,limit}$) and a maximum limit value ($\theta_{jmax,limit}$).

If $\theta_j < \theta_{jmin}$ then the joint position percentage $\Delta\theta$ is provided by Equation 10.

$$\text{If, } \Delta\theta = \frac{\theta_{jmin} - \theta_j}{\theta_{jmin} - \theta_{jmin,limit}} \qquad \text{Eq. 10}$$

If $\theta_j > \theta_{jmax}$ then the joint position percentage $\Delta\theta$ is provided by Equation 11.

$$\Delta\theta = \frac{\theta_j - \theta_{jmax}}{\theta_{jmax,limit} - \theta_{jmax}} \qquad \text{Eq. 11}$$

If the joint position percentage $\Delta\theta$ is less than a threshold such as $\Delta\theta < 0.8$, then the torque ratio is provided by Equation 12.

$$r_\tau = \text{sign}(\tau_j) * \sqrt{1 - (c * \Delta\theta - 1)^2} * \sqrt{1 - \left(\frac{|\tau_j| - \tau_{normal}}{|\tau_{jmax}| - \tau_{normal}} - 1\right)^2} \qquad \text{Eq. 12}$$

If the joint position percentage $\Delta\theta$ is greater than the threshold, the torque ratio is provided by Equation 13.

$$r_\tau = \text{sign}(\tau_j) * \sqrt{1 - \left(\frac{|\tau_j| - \tau_{normal}}{|\tau_{jmax}| - \tau_{normal}} - 1\right)^2} \qquad \text{Eq. 13}$$

For equations 12 and 12, sign ($\tau_j$) causes that the sign of torque align with the torque, such that, with a negative torque ratio, the torque is also negative and the articulation joint should not be permitted to move further negative in or order to avoid further increasing of the absolute value of the torque.

The value for c is a predetermined value and may be set by a user or set by the control unit 210. When c=1.125 and $\Delta\theta=0.8$, the term $1-(1.25\Delta\theta-1)^2$ is 1, which guarantees that after the joint is close enough to the joint limit, the torque ratio should fully respond (e.g., 100% percent) on torque changes, and the influence from joints position diminishes. The torque ratio will be guaranteed to be between [−1, 1] and will be a number between (−1, 1), and when the joint position and torque are between the desired handling range defined by the user. The value for c may be set to other values so that the torque responds on torque change and the influence from joint position diminishes at a greater span. In one implementation, c is set to zero when the joint position percentage (Δθ) is below a percentage threshold.

Turning to the adjustment of joint commands, the torque ratio ($r_\tau$) can be applied to individual user commands in specific situations in order to protect the end effector from hardstops. Equation 14 describes that the joint command at time (k+1) is defined by the joint command at time k plus a relative joint command depending on a user input. In other words, for any given current/initial command applied to an actuator for a particular joint, a subsequent user command is summed with the relative joint command in order to adjust the next command applied to the actuator.

$$\theta_{jcmd}(k+1)=\theta_{jcmd}(k)+\theta_{jrelative} \quad \text{Eq. 14}$$

At block 507, a joint command compensation ratio is first calculated based on the torque ratio. The joint command compensation ratio define an amount that user commands for joint position should be adjusted given the state of the joint. At block 509, a relative joint command is calculated. The relative joint command may be based on the joint command compensation ratio and a user command 508.

This process of controlling the joint is modified according to the torque ratio ($r_\tau$) calculated by the control unit 210. When $\theta_{jrelative}$>0 and the torque ratio ($r_\tau$) >0, then equation 15 provides the new joint command based on joint command compensation ratio (1−$r_\tau$). In this case, the relative joint command is e.g., (1−$r_\tau$)*$\theta_{jrelative}$.

When $\theta_{jrelative}$<0 and the torque ratio ($r_\tau$)<0, then equation 16 provides the new joint command based on joint command compensation ratio (1−$r_\tau$). In this case, the relative joint command is e.g., (1+$r_\tau$)*$\theta_{jrelative}$. The relative joint command is an articulation joint adjustment, for the articulation drive disk or the one or more corresponding rotary motors, in response to the torque ratio to compensate for a hardstop.

$$\theta_{jcmd}(k+1)=\theta_{jcmd}(k)+(1-r_\tau)*\theta_{jrelative} \quad \text{Eq. 15}$$

$$\theta_{jcmd}(k+1)=\theta_{jcmd}(k)+(1+r_\tau)*\theta_{jrelative} \quad \text{Eq. 16}$$

In either case, at block 512, a summing point, which may be a logical representation of one or more hardware components, combines the relative joint command and a previous joint command 511 (e.g., $\theta_{jcmd}$(k)).

At block 513, joint position control by the control unit 210 calculates a joint position based on the relative joint command and the previous joint command to determine a position an angle or a position for the articulation joint in order to compensate for the hardstop or collision. The control unit 210 identifies or calculates an initial joint position or a change in joint position. The initial joint position may be determined from a user input. The initial joint position may also consider one or more supplemental positioning algorithms such as calibration, homing, engagement, or hardstop handling to determine an initial position for the joint that deviates from the user input.

Because of the property constants used in calculation of the torque ratio, the articulation joint position is calculated based on a relationship between at least one measured motor position for the one or more corresponding rotary motors and at least one property constant for the surgical tool.

At block 515, motor control by the control unit 210 calculates one or more motor commands in order to move the corresponding actuators to the position or angle determined by the control unit 210. The motor command is provided to the tool driver 230, for example, to control actuators R2 and/or R4. The control unit 210. The control unit 210 may consult a model for the surgical tool 240 that relates motor commands to joint positions for the joint under analysis. The model may depend on the drive train in the surgical tool 240.

Herein, the phrase "coupled with" is defined to mean directly connected to or indirectly connected through one or more intermediate components. Such intermediate components may include both hardware- and software-based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The disclosed mechanisms may be implemented at any logical and/or physical point(s), or combinations thereof, at which the relevant information/data (e.g., message traffic and responses thereto) may be monitored or flows or is otherwise accessible or measurable, including one or more gateway devices, modems, computers or terminals of one or more market participants, e.g., client computers, etc.

One skilled in the art will appreciate that one or more modules described herein may be implemented using, among other things, a tangible computer-readable medium comprising computer-executable instructions (e.g., executable software code). Alternatively, modules may be implemented as software code, firmware code, specifically configured hardware or processors, and/or a combination of the aforementioned.

The operations of computer devices and systems shown in FIGS. 1-25 may be controlled by computer-executable instructions stored on a non-transitory computer-readable medium. For example, the exemplary computer device or control unit 210 may store computer-executable instructions, generate electronic messages, extracting information from the electronic messages, executing actions relating to the electronic messages, and/or calculating values from the electronic messages to facilitate any of the algorithms or acts described herein. Numerous additional servers, computers, handheld devices, personal digital assistants, telephones, and other devices may also be connected to control unit 210.

As illustrated in FIG. 12, the computer system may include a processor 312 implemented by a central processing unit (CPU), a graphics processing unit (GPU), or both. The processor 312 may be a component in a variety of systems. For example, the processor 312 may be part of a standard personal computer or a workstation. The processor 312 may be one or more general processors, digital signal processors, specifically configured processors, application specific integrated circuits, field programmable gate arrays, servers, networks, digital circuits, analog circuits, combinations thereof, or other now known or later developed devices for analyzing and processing data. The processor 312 may implement a software program, such as code generated manually (i.e., programmed).

The computer system includes memory 314 that can communicate via a bus. The memory 314 may be a main memory, a static memory, or a dynamic memory. The memory 314 may include, but is not limited to, computer-readable storage media such as various types of volatile and non-volatile storage media, including but not limited to random-access memory, read-only memory, programmable read-only memory, electrically programmable read-only memory, electrically erasable read-only memory, flash memory, magnetic tape or disk, optical media and the like. In one embodiment, the memory 314 includes a cache or random-access memory for the processor 312. In alternative embodiments, the memory 314 is separate from the processor 312, such as a cache memory of a processor, the system memory, or other memory. The memory 314 may be an external storage device or database for storing data. Examples include a hard drive, compact disk ("CD"), digital video disc ("DVD"), memory card, memory stick, floppy disk, universal serial bus ("USB") memory device, or any other device operative to store data. The memory 314 is operable to store instructions executable by the processor 312. The functions, acts or tasks illustrated in the figures or described herein may be performed by the programmed processor 312 executing the instructions stored in the memory 314. The functions, acts or tasks are independent of the particular type of instructions set, storage media, processor or processing strategy and may be performed by software, hardware, integrated circuits, firmware, microcode, and the like, operating alone or in combination. Likewise, processing strategies may include multiprocessing, multitasking, parallel processing, and the like.

The computer system may further include a display unit 319, such as a liquid crystal display (LCD), an organic light emitting diode (OLED), a flat panel display, a solid-state display, a cathode ray tube (CRT), a projector, a printer or other now known or later developed display device for outputting determined information. The display 319 may act as an interface for the user to see the functioning of the processor 312, or specifically as an interface with the instructions stored in the memory 314 or elsewhere in the control unit 210.

Additionally, the computer system may include an input device 317 configured to allow a user to interact with any of the components of system. The input device 317 may be a number pad, a keyboard, or a cursor control device, such as a mouse, or a joystick, touch screen display, remote control, or any other device operative to interact with the control unit 210. The input device 317 may receive tool position controls from a user. The tool position controls may be applied to one or more of the actuators described above. The input device 317 may also receive settings or configurations include the physical constants a and b and/or the predetermined constant c for tuning the hardstop handling. The input device 317 may receive one or more bounds for defining the outer range 523, the middle range 521, and the inner range 521 such as values for $\theta_{jmin}$, $\theta_{jmax}$, $\theta_{jmin,limit}$ and $\theta_{jmax,limit}$.

The present disclosure contemplates a computer-readable medium that includes instructions or receives and executes instructions responsive to a signal, so that a device connected to a network can communicate voice, video, audio, images, or any other data over the network. Further, the instructions may be transmitted or received over the network via a communication interface 318. The communication interface 318 may be a part of the processor 312 or may be a separate component. The communication interface 218 may be a physical connection in hardware. The communication interface 318 is configured to connect with a network, external media, the display unit 319, or any other components in the system, or combinations thereof. The connection with the network may be a physical connection, such as a wired Ethernet connection or may be established wirelessly. Likewise, the additional connections with other components of the system may be physical connections or may be established wirelessly.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the described embodiments should not be understood as requiring such separation in all embodiments, and it should be understood that the described program components and systems can generally be integrated together in a single software product or packaged into multiple software products.

What is claimed is:

1. An apparatus to compensate for collision between an end effector of a surgical tool and a hardstop, the apparatus comprising:
   a tool driver connected by a shaft to the end effector, the tool driver having at least an articulation drive disk driven by one or more corresponding rotary motors, the articulation drive disk corresponding to an articulation motion of the end effector in a plane corresponding to a longitudinal axis of the shaft connecting the tool driver to the end effector; and
   one or more processors configured to:
      calculate an articulation joint position for the articulation drive disk or the one or more corresponding rotary motors;
      calculate an articulation joint torque for the articulation drive disk or the one or more corresponding rotary motors;

determine a torque ratio based on the articulation joint position and the articulation joint torque; and calculate an articulation joint adjustment, for the articulation drive disk or the one or more corresponding rotary motors, in response to the torque ratio to compensate for a hardstop.

2. The apparatus of claim 1, the one or more processors configured to:

adjust a user command using the articulation joint adjustment; and provide the adjusted user command to the tool driver.

3. The apparatus of claim 1, wherein the articulation joint position is calculated based on a relationship between at least one measured motor position for the one or more corresponding rotary motors and at least one property constant for the surgical tool.

4. The apparatus of claim 3, wherein the relationship for the joint position ($\theta_j$) is provided by:

$$\theta_j = \sin^{-1} \frac{a + \frac{1}{2}(\theta_{m1} + \theta_{m2})}{b},$$

wherein the at least one measured motor position includes a first motor position ($\theta_{m1}$) for a first motor of the one or more corresponding rotary motors and a second motor position ($\theta_{m2}$) for a second motor of the one or more corresponding rotary motors, and the at least one property constant includes first constant a and second constant b.

5. The apparatus of claim 1, the articulation joint torque is calculated based on a relationship at least one measured torque for the one or more corresponding rotary motors and at least one property constant for the surgical tool.

6. The apparatus of claim 5, wherein the relationship for the joint torque ($\tau_j$) is provided by:

$$\tau_j = \frac{b}{a}(\tau_{m1} + \tau_{m2}) * \sqrt{1 - \frac{a}{b}(\tau_{m1} + \tau_{m2})^2},$$

wherein the at least one measured torque includes a first torque ($\tau_{m1}$) for a first motor of the one or more corresponding rotary motors and a second torque ($\tau_{m2}$) for a second motor of the one or more corresponding rotary motors, and the at least one property constant includes first constant a and second constant b.

7. The apparatus of claim 1, wherein the relationship for the joint torque ($\tau_j$) is based on static force analysis.

8. The apparatus of claim 1, wherein the torque ratio is determined based on at least one comparison between the joint position and a position threshold or at least one comparison between the joint torque and a torque threshold.

9. The apparatus of claim 1, the one or more processors configured to:

calculate a joint position percentage ($\Delta\theta$) when the joint position is within a compensation range bounded by a minimum value ($\theta_{jmin}$) and a maximum value ($\theta_{jmax}$) and outside of an out of bounds range bounded by a minimum limit value ($\theta_{jmin,limit}$) and a maximum limit value ($\theta_{jmax,limit}$).

10. The apparatus of claim 9, wherein the joint position percentage ($\Delta\theta$) is:

$$\frac{\theta_{jmin} - \theta_j}{(\theta_{jmin} - \theta_{jmin,limit})} \text{ when } \theta_j < \theta_{jmin} \text{ or}$$

$$\frac{\theta_j - \theta_{jmax}}{(\theta_{jmax,limit} - \theta_{jmax})} \text{ when } \theta_j > \theta_{jmax}.$$

11. The apparatus of claim 10, wherein the torque ratio ($r_\tau$) is determined based on $$r_\tau = \text{sign}(\tau_j) * \sqrt{1 - (c*\Delta\theta - 1)^2} * \sqrt{1 - \left(\frac{|\tau_{joint}| - \tau_{jnormal}}{|\tau_{joint}| - \tau_{jnormal}} - 1\right)^2},$$

wherein a constant c is a predetermined value.

12. The apparatus of claim 11, wherein c is set to zero when the joint position percentage ($\Delta\theta$) is below a percentage threshold.

13. A method to compensate for collision between an end effector of a surgical tool and a hardstop, the method comprising:

calculating an articulation joint position for an articulation drive disk or one or more corresponding rotary motors corresponding rotary motors for an articulation motion of the end effector in a plane corresponding to a longitudinal axis of a shaft connecting the end effector;

calculating an articulation joint torque for the articulation drive disk or the one or more corresponding rotary motors corresponding rotary motors;

determining a torque ratio based on the articulation joint position and the articulation joint torque; and calculating an articulation joint adjustment in response to the torque ratio to compensate for a hardstop.

14. The method of claim 13, further comprising:

adjusting a user command using the articulation joint adjustment; and providing the adjusted user command to the articulation drive disk.

15. The method of claim 13, wherein the articulation joint position is calculated based on a relationship between at least one measured motor position for the one or more corresponding rotary motors and at least one property constant for the surgical tool.

16. The method of claim 13, the articulation joint torque is calculated based on a relationship at least one measured torque for the one or more corresponding rotary motors and at least one property constant for the surgical tool.

17. The method of claim 13, further comprising:

calculating a joint position percentage ($\Delta\theta$) when the joint position is inside a compensation range bounded by a minimum value ($\theta_{jmin}$) and a maximum value ($\theta_{jmax}$) and outside of an out of bounds range bounded by a minimum limit value ($\theta_{jmin,limit}$) and a maximum limit value ($\theta_{jmax,limit}$).

18. The method of claim 17, wherein the joint position percentage ($\Delta\theta$) is:

$$\frac{\theta_{jmin} - \theta_j}{(\theta_{jmin} - \theta_{jmin,limit})} \text{ when } \theta_j < \theta_{jmin} \text{ or}$$

$$\frac{\theta_j - \theta_{jmax}}{(\theta_{jmax,limit} - \theta_{jmax})} \text{ when } \theta_j > \theta_{jmax}.$$

19. The method of claim 18, wherein the torque ratio ($r_\tau$) is determined based on $$r_\tau = \text{sign}(\tau_j) * \sqrt{1 - (c*\Delta\theta - 1)^2} * \sqrt{1 - \left(\frac{|\tau_{joint}| - \tau_{jnormal}}{|\tau_{joint}| - \tau_{jnormal}} - 1\right)^2},$$

wherein a constant c is a predetermined value.

20. An apparatus to compensate for collision between an end effector of a surgical tool and a hardstop, the apparatus comprising:
- a tool driver connected by a shaft to the end effector, the tool driver having a first articulation drive disk driven by a first motor and a second articulation disk driven by a second motor, wherein the first articulation drive disk and the second articulation disk cooperate to move the end effector in a plane corresponding to a longitudinal axis of the shaft connecting the tool driver to the end effector; and
- one or more processors configured to:
    - calculate an articulation joint position for the first motor or the second motor;
    - calculate an articulation joint torque for the first motor or the second motor;
    - determine a torque ratio based on the articulation joint position and the articulation joint torque; and
    - adjust a commanded articulation joint position received from a user based on the torque ratio to compensate for collision involving the end effector.

* * * * *